United States Patent
Worm et al.

(10) Patent No.: US 12,268,763 B2
(45) Date of Patent: Apr. 8, 2025

(54) CURABLE DENTAL TWO-PACK COMPOSITION

(71) Applicant: DENTSPLY SIRONA INC., York, PA (US)

(72) Inventors: Matthias Worm, Singen (DE); Joachim E. Klee, Radolfzell (DE); Helmut Ritter, Bensheim (DE); Özgür Capar, Bensheim (DE); Laura Hartmann, Bensheim (DE); Moniralsadat Tabatabai, Bensheim (DE)

(73) Assignee: Dentsply Sirona Inc., York, PA (US)

( * ) Notice: Subject to any disclaimer, the term of this patent is extended or adjusted under 35 U.S.C. 154(b) by 809 days.

(21) Appl. No.: 17/291,337

(22) PCT Filed: Nov. 8, 2019

(86) PCT No.: PCT/EP2019/080733
§ 371 (c)(1),
(2) Date: May 5, 2021

(87) PCT Pub. No.: WO2020/094859
PCT Pub. Date: May 14, 2020

(65) Prior Publication Data
US 2022/0000723 A1    Jan. 6, 2022

(30) Foreign Application Priority Data

Nov. 8, 2018   (EP) .................................... 18205107

(51) Int. Cl.
*A61K 6/891* (2020.01)
*A61K 6/54* (2020.01)
(Continued)

(52) U.S. Cl.
CPC ............... *A61K 6/891* (2020.01); *A61K 6/54* (2020.01); *A61K 6/77* (2020.01); *A61K 6/831* (2020.01)

(58) Field of Classification Search
CPC .......... A61K 6/54; A61K 6/891; C08L 79/02; C08L 101/005
See application file for complete search history.

(56) References Cited

U.S. PATENT DOCUMENTS

| | | |
|---|---|---|
| 3,655,605 A | 4/1972 | Smith |
| 3,814,717 A | 6/1974 | Wilson |

(Continued)

FOREIGN PATENT DOCUMENTS

| | | | | |
|---|---|---|---|---|
| EP | 0673637 A1 * | 3/1995 | ............... | A61K 6/00 |
| EP | 2813497 A1 * | 12/2014 | ........... | C07D 317/36 |

(Continued)

OTHER PUBLICATIONS

"Glass Ionomer Cement Formulations: I. The preparation of Novel Fluoroaluminosilicate Glasses High in Fluorine"; Brian E. Kent et. al.; Journal of Dental Research; vol. 58 Issue 6; Jun. 1979; pp. 1607-1619.

(Continued)

*Primary Examiner* — Peter A Salamon
(74) *Attorney, Agent, or Firm* — SCHWEGMAN LUNDBERG & WOESSNER, P.A.

(57) ABSTRACT

The present invention is related to a curable dental two-pack composition comprising:
- (a) a first paste comprising (a-1) one or more crosslinker having at least four primary amino groups; and
- (b) a second paste comprising (b-1) one or more compounds polymerizable with a crosslinker of the first paste in a step-growth polymerization reaction;

(Continued)

wherein (b-1) the compound polymerizable with the crosslinker compounds is a compound of the following formula (II):

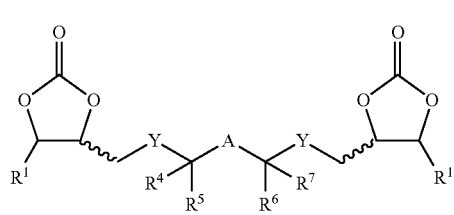

wherein
A is a hydrocarbon group which may contain one or more hetero atoms selected from oxygen and sulfur atoms;
$R^1$ is as defined in claim 1;
$R^4$, $R^5$, $R^6$ and $R^7$ are independent from each other and represent
a hydrogen atom or a methyl group and
the Y, which are independent from each other represent
a single bond, an oxygen atom, a sulfur atom, an ester bond or a urethane bond.

15 Claims, 2 Drawing Sheets

(51) Int. Cl.
  *A61K 6/77* (2020.01)
  *A61K 6/831* (2020.01)

(56) References Cited

U.S. PATENT DOCUMENTS

| | | |
|---|---|---|
| 4,143,018 A | 3/1979 | Crisp |
| 4,209,434 A | 6/1980 | Crisp |
| 4,360,605 A | 11/1982 | Schmitt |
| 4,376,835 A | 3/1983 | Schmitt |
| 4,814,362 A | 3/1989 | Billington |
| 5,318,929 A | 6/1994 | Jana |
| 5,360,770 A | 11/1994 | Chadwick |
| 7,700,666 B2 * | 4/2010 | Bissinger ............ A61K 6/90 523/109 |
| 2004/0079258 A1 | 4/2004 | Hoescheler |
| 2008/0287566 A1 | 11/2008 | Musikant et al. |

FOREIGN PATENT DOCUMENTS

| | | |
|---|---|---|
| EP | 3650004 A1 | 5/2020 |
| WO | WO-2020094859 A1 | 5/2020 |

OTHER PUBLICATIONS

International Search Report; PCT/EP2019/080733; Jan. 13, 2020 (completed); Jan. 24, 2020 (mailed).
Written Opinion of the International Searching Authority; PCT/EP2019/080733; Jan. 13, 2020 (completed); Jan. 24, 2020 (mailed).
International Preliminary Report on Patentability; PCT/EP2019/080733; Jan. 13, 2020 (completed); Jan. 24, 2020 (mailed).
"Poly(propylene imine) Dendrimers: Large-Scale Synthesis by Heterogeneously Catalyzed Hydrogenations"; Ellen M. M. De Brabander-Van Den Berg et al.; Angewandte Chemie, International Ed; vol. 32, No. 9 ; pp. 1308-1311.
Polyethylenimine CAS 25987-06-8, (Dec. 1, 2017), XP055657223; Anonymous: Retrieved from the Internet: URL: https:// www.chemicalbook.com/ChemicalProductProperty_EN_CB5499238.htm.
"N,N,N',N'-tetrakis(3-aminopropyl)butane-1,4-diamine / Chemsrc"; CAS#: 120239-63-6 I, (Jun. 21, 2019), XP055657214; Anonymous: Retrieved from the Internet: URL:https://www.chemsrc.com/en/cas/120239-63-6 852593.html.
"European Application Serial No. 18205107.8, Extended European Search Report mailed Jun. 19, 2019", 7 pgs.
"European Application Serial No. 18205107.8, Noting of loss of rights pursuant to Rule 112(1) EPC mailed Dec. 8, 2020", 2 pgs.

* cited by examiner

CURABLE DENTAL TWO-PACK COMPOSITION

FIELD OF THE INVENTION

The present invention relates to a curable dental two-pack composition. The curable dental two-pack composition comprises a crosslinker having at least four primary amino groups and a compound polymerizable with said crosslinker in a step-growth polymerization reaction. A compound polymerizable with the crosslinker has at least two optionally substituted 1,3-dioxolan-2-one groups attached to or connected by one or more organic groups. The curable dental two-pack composition may be a root canal sealing composition or a pulp capping composition.

Furthermore, the present invention relates to a use of a crosslinker having at least four primary amino groups for the preparation of a curable dental two-pack composition selected from a root canal sealing composition and a pulp capping composition.

The polymerizable compound contained in the curable dental two-pack composition according to the present invention allows to replace bisphenol-A based components such a bisphenol A diglycidyl ether in a root canal sealing composition or pulp capping composition due to favourable thermomechanical properties of the cured compositions and low viscosity of the uncured compositions, as well as small dimensional changes of the compositions upon curing.

BACKGROUND OF THE INVENTION

Dental compositions are desired to approach natural tooth structure with regard to strength and appearance. Accordingly, a great effort is documented by the prior art, which is directed to the development of dental compositions having improved properties with regard to physical properties, biocompatibility, aesthetics and handling properties.

Dental compositions selected from a root canal sealing composition and a pulp capping composition are subject to additional requirements in that the cured product is required to have a high radiopacity and in that the composition may not require external irradiation for curing. Moreover, it is desirable that the composition adheres to the wall of the root canal in order to further improve the tight sealing of the dental root canal. Given that the shape of the root canal may change as a result to mastication and temperature changes, the cured composition must tolerate such changes without compromising a tight seal of the root canal.

Accordingly, in order to provide such additional properties, a root canal sealing composition or pulp capping composition contains radiopaque particulate fillers dispersed in a curable matrix. However, the dispersion of radiopaque particulate fillers gives rise to a stability problem of the dispersions due to the high density of the filler and the low viscosity of the curable matrix.

Moreover, in order to be able to cure a root canal sealing composition or pulp capping composition in the absence of light, the composition is cured by a thermal curing mechanism which may involve step growth polymerizing epoxide precursor compounds such as bisphenol A diglycidyl ether. Bisphenol A diglycidyl ether provides an excellent combination of properties for the purpose of a dental compositions. Specifically, favourable mechanical properties of the cured compositions while the viscosity of the uncured compositions may be adjusted to be comparably low, and a low shrinkage of the compositions upon curing are reasons for the widespread use of bisphenol A based materials in the dental field.

However, epoxide precursors may be irritants and are problematic with regard to carcinogenicity and mutagenicity.

Moreover, bisphenol A is a known endocrine disrupter which can mimic estrogen and may lead to negative health effects. More specifically, bisphenol A mimics the structure and function of the hormone estradiol with the ability to bind to and activate the same estrogen receptor as the natural hormone. Based on the functional relevance of bisphenol-A it is considered that bisphenol-A might contribute to the development of breast cancer. Accordingly, regulatory bodies might determine safety levels of bisphenol-A for humans so that the use of bisphenol A based materials containing bisphenol A in a dental composition cannot be continued in the future.

In order to maintain a tight seal of the root canal, the thermomechanical properties must be adjusted so that the cured composition shows flexibility in case of dimensional changes of the root canal due to mastication or temperature changes. For this purpose, a glass transition temperature close to the body temperature is desirable.

EP 0 673 637 discloses a two-paste dental filling composition useful as a root canal sealer. A first paste is obtained by mixing diglycidyl ether of bisphenol-A, diglycidyl ether of bisphenol-F, $CaWO_4$, $ZrO_2$, $Fe_2O_3$ and Aerosil 200. A second paste is prepared by mixing 1-amino-adamantante, N,N'-dibenzyl-5-oxanonanediamine, Aerosil 200, $CaWO_4$, $ZrO_2$ and a silicon oil. The composition has a long setting time of 8 hours (at 37° C.) and the working time is 16 hours at (23° C.), respectively. The $T_g$ of a generic composition is about 45° C. The pastes are mixed at a ratio of 1:1 by volume, which is desirable in view of using a two-barrel mixing syringe. The compositions according to EP 0 673 637 may be considered as a gold standard for root canal sealing compositions.

In order to increase the curing rate of the composition, EP 2 813 497 A1 discloses a dental root canal sealing composition, comprising: (a) a radioopaque particulate filler; (b) a monomer having at least two groups selected from primary and secondary amino groups and thiol groups; and (c) a compound polymerizable with the monomer (b) in a step-growth polymerization reaction based on at least two 1,3-dioxolan-2-one groups. The gel time at 37° C. of a stoichiometric mixture of bis-(2,3-carbonatopropyl)-2,2,4 or 2,4,4 trimethyl-hexamethylene dicarbamate and hexamethylene diamine was found to be 20-30 min. However, the resin composition has a dynamic viscosity in the order of about 3000 Pas (25° C.) which is higher than a more desirable dynamic viscosity in the range of 1 to 10 Pas (25° C.), in particular when the pastes are adapted for mixing at a ratio of 1:1.

Objective of the Present Invention

It is the problem of the present invention to provide a curable dental two-pack composition having properties including physical properties of the cured composition, dispersion stability and handling properties of the uncured composition, and biocompatibility, which are at least on the level of corresponding bisphenol A based materials, while the bisphenol-A component is replaced, in particular in a dental root canal sealer composition or a pulp capping composition.

The uncured compositions should have viscosities, in particular when formulated at a mixing ratio of the pastes of 1:1 by volume, which are improved compared to the compositions according to EP 2 813 497 A1.

Additionally, curing rates should be high. Specifically, the curing rate of the dental two-pack compositions should be higher than the curing rate of bisphenol-A containing dental compositions known in the prior art EP 0 673 637.

The compositions should show good thermomechanical properties for stable adhesion to the wall of a dental root canal in order to further improve the tight sealing of the root canal.

It is a further problem of the present invention to provide a curable dental two-pack composition selected from a root canal sealing composition and a pulp capping composition which is cost efficient and simple and available on a scale which is industrially relevant.

SUMMARY OF THE INVENTION

According to a first aspect, the present invention provides a curable dental two-pack composition comprising:
(a) a first paste comprising (a-1) one or more crosslinkers having at least four primary amino groups; and
(b) a second paste comprising (b-1) one or more compounds polymerizable with a crosslinker of the first paste in a step-growth polymerization reaction which have at least two 1,3-dioxolan-2-one groups selected from the following formula (A) and (B) attached to or connected by one or more organic groups:

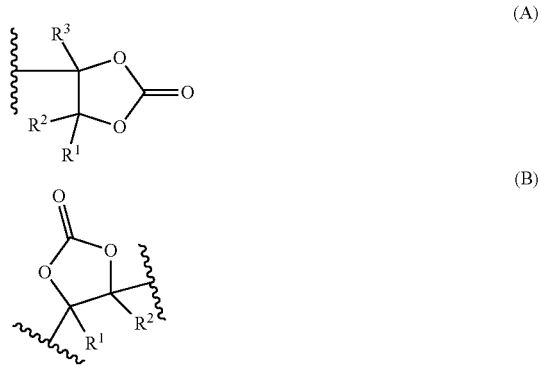

wherein R1, R2 and R3, which are independent from each other, represent a hydrogen atom or a $C_{1-6}$ alkyl group; wherein (b-1) the compound polymerizable with the crosslinker compounds is a compound of the following formula (II):

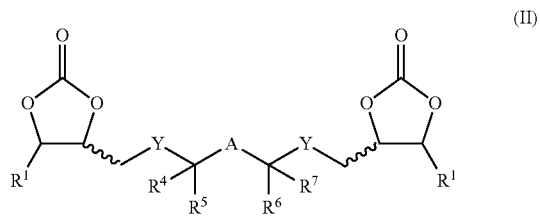

wherein
A is a hydrocarbon group which may contain one or more hetero atoms selected from oxygen and sulfur atoms;

$R^1$ is a hydrogen atom or a $C_{1-6}$ alkyl group;
$R^4$, $R^5$, $R^6$ and $R^7$ are independent from each other and represent a hydrogen atom or a methyl group and
the Y, which are independent from each other represent a single bond, an oxygen atom, a sulfur atom, an ester bond or a urethane bond.

According to a second aspect, the present invention provides a curable dental two-pack composition according to the first aspect of the present invention, wherein the first paste further comprises:
(a-2) one or more compounds having two groups selected from primary and secondary amino groups.

According to a third aspect, the present invention provides a curable dental two-pack composition according to the first or the second aspect of the present invention further comprising:
(c) a particulate filler not containing amino groups.

According to a fourth aspect, the present invention provides a curable dental two-pack composition according to any one of the preceding aspects of the present invention which is a dental root canal sealer composition or a pulp capping composition.

According to a fifth aspect, the present invention provides a curable dental two-pack composition according to any one of the preceding aspects which is packaged in a two-barrel syringe, whereby the volume ratio of the pastes is preferably in the range of 0.9 to 1.1:1, more preferably 1:1.

According to a sixth aspect, the present invention provides a use of the crosslinker according the first aspect of the present invention for the preparation of a curable dental two-pack composition selected from a root canal sealing composition and a pulp capping composition.

The present invention is based on the recognition that a polymerizable compound having at least two optionally substituted 1,3-dioxolane-2-one groups attached to or connected by one or more organic groups, preferably through a methyleneoxy ($CH_2O$—) linkage, provides an excellent combination of properties for the purpose of a dental two-pack composition selected from a root canal sealing composition and a pulp capping composition when polymerized in the presence of a crosslinker having at least four primary amino groups in a step-growth polymerization reaction. Specifically, favourable thermomechanical properties of the cured compositions, low viscosity, good handling properties and high dispersion stability of the uncured compositions as well as low dimensional changes of the compositions upon curing allow the replacement of bisphenol-A diglycidyl ether based materials and other epoxides in the preparation of a root canal sealing composition or pulp capping composition, while at the same time providing high curing rate and short gel time.

BRIEF DESCRIPTION OF THE FIGURES

For a more complete understanding of the present invention, reference is made to the following Detailed Description of the Invention considered in conjunction with the accompanying figures, in which.

DETAILED DESCRIPTION OF THE INVENTION

Figure 1:
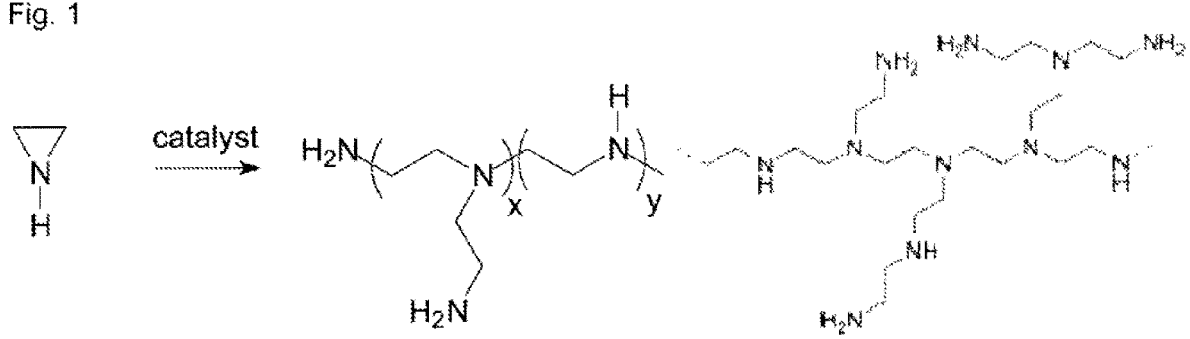
FIG. 1 shows the synthesis of a hyperbranched polyethylene imine crosslinker according to the present invention, which have at least four primary amino groups.

A "crosslinker having at least four primary amino groups" is a compound, polymer or particle formally derived from at least four molecules of ammonia whereby a single hydrogen atom of each ammonia molecule is replaced by an organic group, polymer, or particle whereby the resulting at least four primary amino groups are covalently linked to a single crosslinker structure.

The term "organic group" relates to a group having a total of 1 to 40 carbon atoms, preferably 2 to 20 carbon atoms. The organic group may include an aliphatic, alicyclic, or aromatic moiety or a combination of two or more of such moieties. The organic group may further include one or more functional groups such as amide groups, ester groups, urethane groups, urea groups, keto groups, ether groups, thioether groups, secondary amino groups, or tertiary amino groups, which link two or more aliphatic, alicyclic, or aromatic moieties, or attach a 1,3-dioxolan-2-one group to the organic group. Furthermore, the organic group may be substituted by one or more substituents selected from hydroxyl groups, halogen atoms or carboxylic acid groups.

An aliphatic group may be saturated or unsaturated. Preferably, the aliphatic group is saturated. Examples of aliphatic groups include alkyl groups. According to the invention, a $C_{1-40}$ alkyl group can include straight or branched alkyl groups having 1 to 40 carbon atoms, preferably 1 to 10 carbon atoms, for example, methyl, ethyl, n-propyl, isopropyl, n-butyl, isobutyl, sec-butyl, tert-butyl, n-pentyl, isopentyl and n-hexyl.

An alicyclic group may be saturated or unsaturated. Preferably, the alicyclic group is saturated. The alicyclic group may include, for example, a $C_{3-6}$ carbocyclic aliphatic ring, a $C_{3-6}$ heterocyclic aliphatic ring, a $C_{3-6}$ saturated aliphatic ring, or a $C_{3-6}$ unsaturated aliphatic ring. Examples of alicyclic groups include cycloalkyl or cycloalkylalkyl groups. A cycloalkyl group may be a $C_{3-6}$ cycloalkyl group. Examples of the cycloalkyl group can include those having 3 to 6 carbon atoms, for example, cyclopropyl, cyclobutyl, cyclopentyl and cyclohexyl. A cycloalkylalkyl group can include those having 4 to 8 carbon atoms. Examples for a cycloalkylalkyl group can include a combination of a straight or branched alkyl group having 1 to 6 carbon atoms and a cycloalkyl group having 3 to 6 carbon atoms. Examples of the cycloalkylalkyl group can for example, include methylcyclopropyl, methylcyclobutyl, methylcyclopentyl, methylcyclohexyl, ethylcyclopropyl, ethylcyclobutyl, ethylcyclopentyl, ethylcyclohexyl, propylcyclopropyl, propylcydobutyl, and propylcyclopentyl. An aromatic group may include a phenyl group or a naphthyl group.

The present invention provides a curable dental two-pack composition. The curable dental two-pack composition may be generally any type of dental composition in which a bisphenol A-free based polymerizable component may be used. Specifically, the curable dental two-pack composition may be selected from a root canal sealing composition or a pulp capping composition. Moreover, the curable dental two-pack composition may also be a dental composite, a dental cement or a dental adhesive.

The curable dental two-pack composition comprises a specific crosslinker (a-1), which has at least four primary amino groups. The crosslinker may be an organic group or polymer, each having at least four primary amino groups, or a nanoparticle displaying on its surface at least four organic groups, wherein each organic group links at least one primary amino group to the nanoparticle.

Preferably, the crosslinker (a-1) having at least four primary amino groups is an organic group having at least four primary amino groups or a polymer having at least four primary amino groups. According to a specific embodiment, the crosslinker (a-1) is a polymer having at least four primary amino groups.

Figure 3:
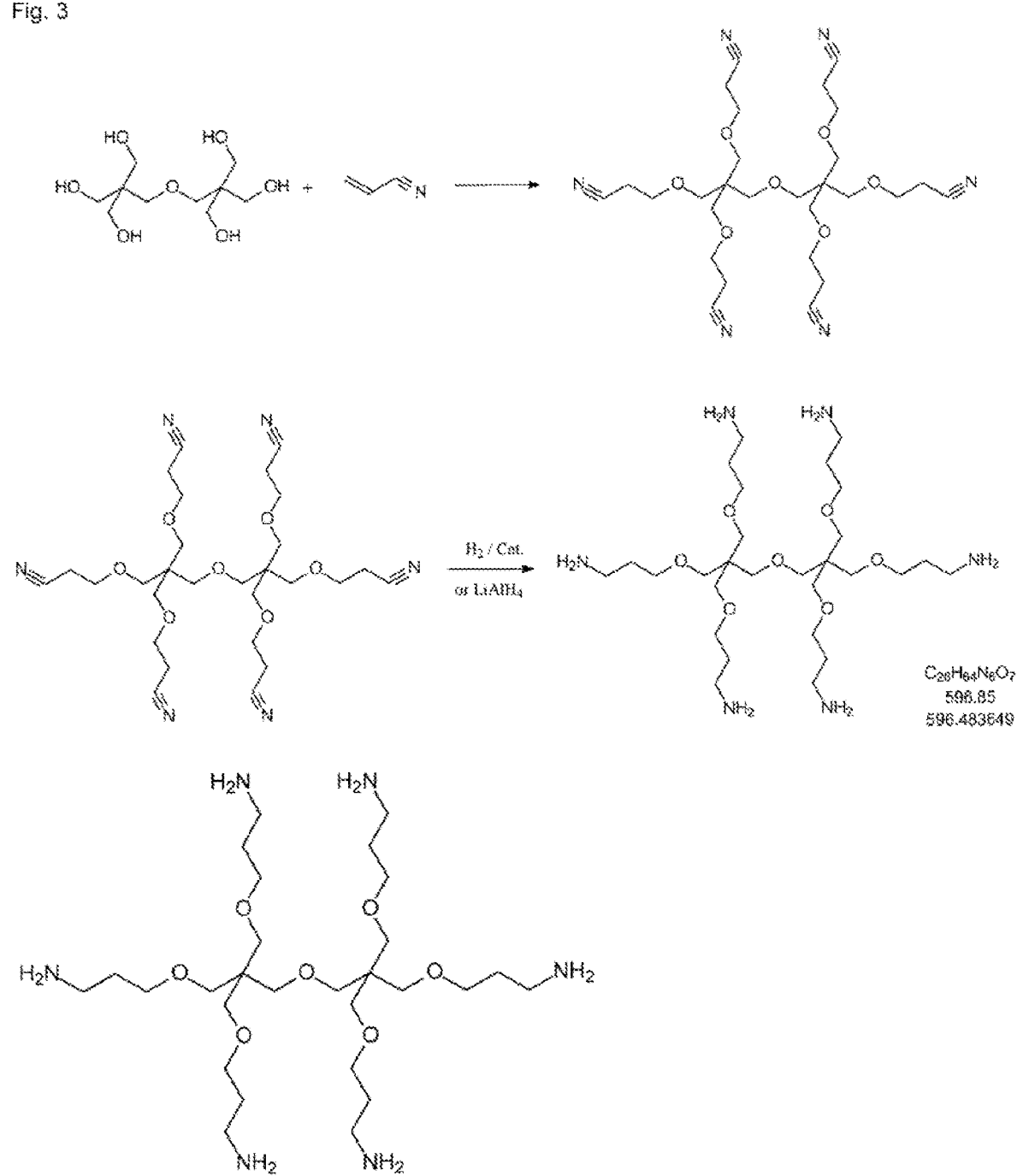
FIG. 3 shows the synthesis of a branched crosslinker having at least four primary amino groups according to the present invention.

If the crosslinker (a-1) is an organic group having at least four primary amino groups, the organic group preferably is a tetravalent saturated or unsaturated aliphatic $C_{1-40}$ hydrocarbon group, notably a saturated aliphatic $C_{4-30}$ hydrocarbon group, which may include one or more functional groups such as ether groups, amide groups, ester groups, urethane groups, urea groups, keto groups, thioether groups, secondary amino groups, or tertiary amino groups, which link two or more aliphatic, alicyclic, or aromatic moieties. Preferably, the organic group is a tetravalent saturated aliphatic $C_{6-20}$ hydrocarbon group which may include one or more functional groups such as ether groups, amide groups, ester groups, urethane groups, which link two or more aliphatic or alicyclic moieties. Furthermore, the organic group may be unsubstituted or substituted by one or more substituents selected from hydroxyl groups, halogen atoms or carboxylic acid groups. The crosslinker (a-1) having at least four primary amino groups may be a linear or branched crosslinker. Preferably, the crosslinker (a-1) having at least four primary amino groups is a branched crosslinker. The crosslinker (a-1) may be synthesized according to the scheme shown FIG. 3. Accordingly, a polyol having four or more hydroxyl group may be reacted with acrylonitrile in a Michael addition reaction and the cyano groups of the reaction product may be reduced to provide a crosslinker having at least four primary amino groups. Furthermore, an Aza-Michael or Michal addition reaction with acrylonitrile and subsequent reduction to amines is possible. Another possibility is the reaction of a polyhalogen or polyepoxide compounds with an excess of $NH_3$.

Specific examples of the crosslinker include the following, wherein R is preferably a saturated aliphatic group:

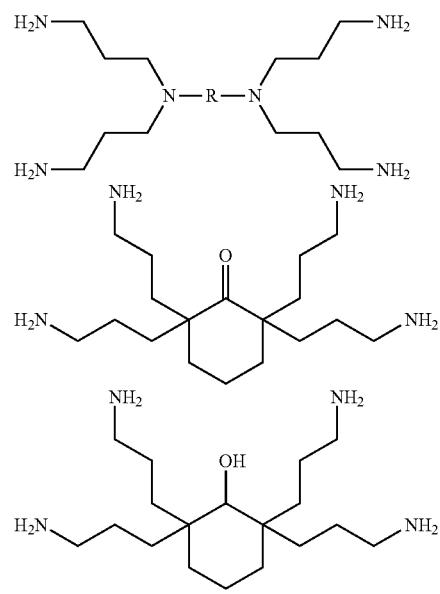

-continued

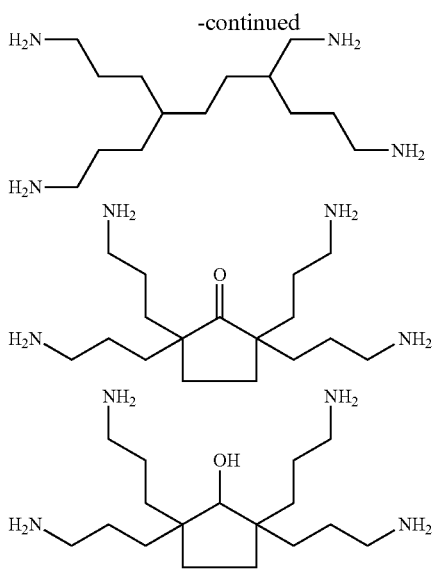

If the crosslinker (a-1) is a polymer having at least four primary amino groups, preferably the crosslinker (a-1) is a linear or branched polyamine obtainable b a polymerization reaction. More preferably, the crosslinker (a-1) is a branched polyamine, which may be a compound of the following formula (I):

wherein
R is an n-valent saturated or unsaturated aliphatic, cycloaliphatic or araliphatic group which may contain one or more hetero atoms selected from oxygen, nitrogen and sulfur atoms,
the Z which may be the same or different, independently represent

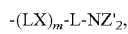

wherein Z' may independently have the same meaning as Z or represents a hydrogen atom,
the L, which may be the same or different, independently represent a single bond, or a saturated aliphatic group,
the X, which may be the same or different, independently represent an oxygen atom, a nitrogen atom or a sulfur atom,
n is an integer of 1 to 20 and
m is an integer of 0 to 4, provided that the compound of formula (I) contains at least four primary amino groups.

According to a preferred embodiment, the crosslinker (a-1) is a branched polyamine compound, wherein the branched polyamine compound is a polyethylene imine. In an even more preferred embodiment, the crosslinker (a-1) is a hyperbranched polyethylene imine as shown in FIG. 1. Most preferably, the crosslinker (a-1) is a hyperbranched polyethylene imine as shown in FIG. 1 with an $M_n$ in the range of from 200 to 3000 g/mol, preferably 400 to 2000 g/mol, in particular $M_n$~1000 g/mol and a viscosity in the range of 0.1 to 25 Pa*s, preferably 1 to 5 Pa*s, in particular η=1.6 Pa*s at 23° C.

The crosslinker may also be a dendrimer, preferably 1. 2. or 3. generation obtainable according to Wömer C. et al. Angew. Chem. 1993, 105(9), 1367-1370, or de Brabander-van den Berg et al. Angew. Chem. 1993, 105(9), 1370-1372.

Figure 2:
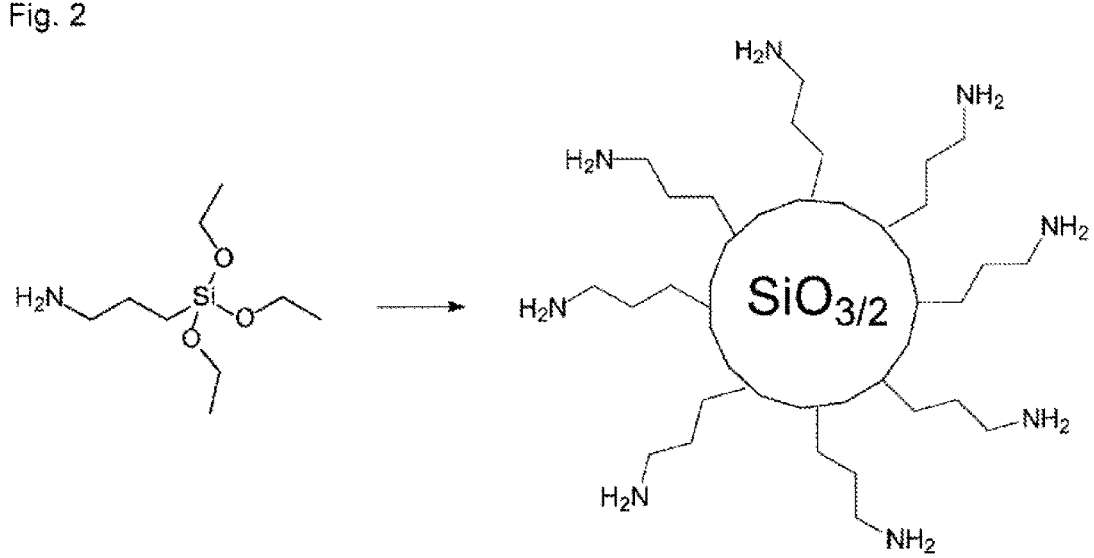
FIG. 2 shows a silica nanoparticle having multiple primary amino groups, which can be used as a crosslinker having at least four primary amino groups according to the present invention.

If the crosslinker (a-1) is a nanoparticle substituted with at least four organic groups, wherein each organic group links at least one primary amino group to the nanoparticle, the nanoparticle may be a silica nanoparticle, an alumina nanoparticle, a zirconia nanoparticle, a titania nanoparticle or a mixed oxide nanoparticle containing two or more metals selected from Si, Al, Zr, and Ti. Additional high atom number metals for increasing the radioopacity may also be incorporated into the mixed oxide, for example, zinc, tungsten or barium. Preferably, an organic group is a saturated aliphatic $C_{1-40}$ hydrocarbon group linking a single primary amino group to the nanoparticle. The crosslinker may be a nanoparticle as shown in FIG. 2.

The curable dental two-pack composition comprises a specific polymerizable compound (b-1) adapted to be polymerized in a step-growth polymerization reaction based on at least two optionally substituted 1,3-dioxolan-2-one groups attached to or connected by one or more organic groups.

The polymerizable compound (b-1) may be obtained as a mixture or composition of stereo- and/or regioisomers depending on the nature of the precursor compounds. For the purpose of the present invention, a mixture or composition of polymerizable compounds (b-1) may be used for preparing a dental two-pack composition. It is also possible to isolate a single stereo- and/or regioisomer of the polymerizable compound (b-1) and to use the isolated single stereo- and/or regioisomer of the polymerizable compound (b-1) for preparing a curable dental two-pack composition of the present invention.

The compound (b-1) is polymerizable with the crosslinker (a-1) in a step-growth polymerization reaction which has at least two groups selected from the following formula (A) and (B) attached to or connected by one or more organic groups:

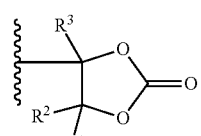

(A)

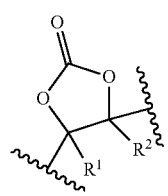

(B)

wherein $R^1$, $R^2$ and $R^3$, which are independent from each other, represent a hydrogen atom or a $C_{1-6}$ alkyl group.

The compound (b-1) step-growth polymerizable with the crosslinker (a-1) or compound (a-2) is a compound of the following formula (II):

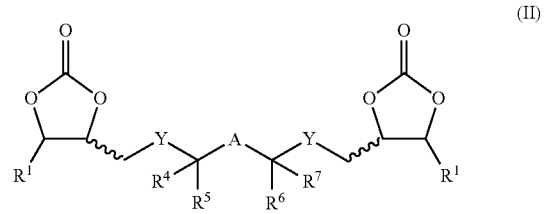

(II)

wherein A is a hydrocarbon group which may contain one or more hetero atoms selected from oxygen, and sulfur atoms; $R^1$ are independent from each other and represent a hydrogen atom or a $C_{1-6}$ alkyl group; $R^4$, $R^5$, $R^6$ and $R^7$ are independent from each other and represent a hydrogen atom or a methyl group and the Y, which are independent from each other represent a single bond, an oxygen atom, a sulfur atom, an ester bond or a urethane bond. Preferably, Y is a bond or an oxygen atom, more preferably an oxygen atom.

In formula (II), A is preferably a straight chain or branched alkylene group or an aromatic group. A $C_{1-20}$ alkylene group can include straight or branched alkyl groups having 1 to 20 carbon atoms, preferably 1 to 10 carbon atoms, for example, methylene, ethylene, n-propylene, isopropylene, n-butylene, isobutylene, sec-butylene, tert-butylene, n-pentylene, isopentylene and n-hexylene. The aromatic group is preferably a phenylene group or a xylylene group which may be substituted by one or more methyl groups.

In another preferred embodiment of the present invention, in formula (II), A is preferably a cyclic $C_{3-6}$ hydrocarbon group, such as a cyclobutyl, a cyclopentyl, a cyclohexyl or a cycloheptyl group; wherein a cyclohexyl group is especially preferred.

A specifically preferred compound (b-1) is thereby cyclohexane-1,4-dimethanol biscyclocarbonate (CHDM-BCC), which has the following formula:

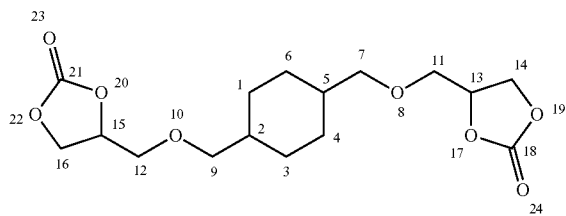 [SMILES: O=C1OCC(COCC2CCC(COCC3COC(=O)O3)CC2)O1]

Another specifically preferred compound (b-1) is neopentyl diglycidyl biscyclocarbonate (NPDG-BCC) 1 which has the following formula:

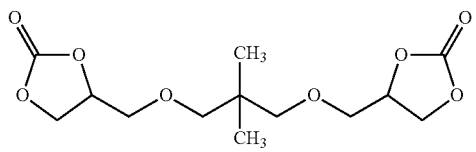

A curable dental two-pack composition contains beside the polymerizable compound of the present invention a further component namely a crosslinker (a-1) having at least four primary amino groups. The advantage of using a crosslinker (a-1) having at least four primary amino groups is a high crosslinking density and thereby favorable mechanical properties.

A curable dental two-pack composition may contain further components, namely one or more compounds (a-2) having two or three groups selected from primary and secondary amino groups.

For some applications, primary diamines are especially useful. Representative diamines include aliphatic diamines such as ethylene diamine, 1,3-diaminopropane, 1,4-diaminobutane, 1,5-diaminopentane, 2-methyl-1,5-diaminopentane, 1,6-diaminohexane, bis(6-aminohexyl)ether, cycloaliphatic diamines such as isophorone diamine, 4,4'-methylene-bis-cyclohexylamine, bis(3-methyl-4-aminocyclohexyl)methane (BMACM), 2,2-bis(3-methyl-4-aminocyclohexyl)propane (BMACP), 2,6-bis(aminomethyl) norbomane (BAMN), and cyclohexane diamine, and heterocyclic diamines such as 3,4 diaminofuran and piperazine. Aromatic diamines such as N,N'-dibenzylethylenediamine, N,N'-dibenzyl-3,6-dioxaoctandiamine-1,8,N,N'-dibenzyl-5-oxanonandiamine-1,9,N,N'-dibenzyl-(2,2,4)/(2,4,4) trimethylhexamethylendiamine, m- or p-phenylenediamine, 2,4- or 2,6-diaminotoluene, and 4,4'-diaminodiphenylmethane may also be used, but are less preferred for toxicological concerns. Therefore, it is preferred to utilize only non-aromatic amines. Mixtures of more than one diamine can also be utilized. Furthermore, in order to adjust the volume ratio of the pastes as a function of the stoichiometry of the reactive groups, it is preferred to use oligomeric or polymeric diamines which are obtainable by reacting a diglycidyl ether with ammonia to prepare the corresponding ß-hydroxy amino compounds.

Triamines include diethylenetriamine, N,N'-dimethyldiethyltriamine, cyclohexyl-1,2,4-triamine. Other triamines such as the Jeffamine® polyoxypropyleneamines available from Huntsman Chemicals, Inc. are also practical. Mixtures of two or more additional compounds (a-2) can also be utilized.

Preferably, the curable dental two-pack composition comprises compounds (b-1), (a-1) and (a-2) in a ratio that the molar ratio of the 1,3-dioxolan-2-one groups (A, B) in component (b-1) in the second paste to the primary amino groups in components (a-1) and (a-2) in the first paste [1,3-dioxolan-2-one groups (b-1)]/[primary amino groups$_{(a\ 1),(a-2)}$] is in the range of from 0.9 to 1.1. If the uncured dental two-pack composition comprises said compounds in said ratio of from 0.9 to 1.1, the cured dental two-pack composition has specifically suitable mechanical properties.

In a preferred embodiment of the curable dental two-pack composition the first paste and the second paste are mixed in equal volumes.

In another preferred embodiment, the curable dental two-pack composition contains the one or more compounds having at least four primary amino groups (a-1) in an amount of from 1 to 40 percent by weight based on the total weight of the composition.

In another preferred embodiment, the curable dental two-pack composition contains the one or more compounds having two groups selected from primary and secondary amino groups (a-2) in an amount of from 1 to 40 percent by weight based on the total weight of the composition.

In another preferred embodiment, the curable dental two-pack composition contains the one or more compounds polymerizable with the crosslinker (b-1) in an amount of from 1 to 40 percent by weight based on the total weight of the composition.

A curable dental two-pack composition may contain further components namely a particulate filler (c) not containing amino groups.

The particulate fillers not containing amino groups may be dental filler(s) known in the art. Preferably, the dental filler(s) are selected from particulate glass fillers and radiopaque fillers. More preferably, the dental filler(s) are selected from radiopaque filler(s).

The term "particulate glass filler" refers to a solid mixture of mainly metal oxides transformed by a thermal melt process into a glass and crushed by various processes. The glass is in particulate form. Moreover, the particulate glass filler may be surface modified, e.g. by silanation or acid treatment.

Preferably, the particulate glass filler is in spherical form.

For the dental fillers, a glass component may be selected from "inert glass(es)", "reactive glass(es)" and "fluoride releasing glass(es)".

The term "inert glass(es)" refers to a glass which is not capable of reacting with a polymer containing acidic groups in a cement reaction. Inert glasses are for example described in the Journal of Dental Research June 1979, pages 1607-1619, or more recently in U.S. Pat. Nos. 4,814,362, 5,318,929, 5,360,770, and application US 2004/0079258 A1. Specifically, from US 2004/0079258 A1, inert glasses are known in which strongly basic oxides such as CaO, BaO, SrO, MgO, ZnO, $Na_2O$, $K_2O$, $Li_2O$ etc. are replaced with weakly basic oxides such as those in the Scandium or Lanthanide series.

The term "reactive glass(es)" refers to a glass which is capable of reacting with a polymer containing acidic groups in a cement reaction. The glass is in particulate form. Any conventional reactive dental glass may be used for the purpose of the present invention. Specific examples of particulate reactive glasses are selected from calcium alumino silicate glass, calcium alumino fluorosilicate glass, calcium aluminumfluoroborosilicate glass, strontium aluminosilicate glass, strontium aluminofluorosilicate glass, strontium aluminofluoroborosilicate glass. Suitable reactive glasses may be in the form of metal oxides such as zinc oxide and/or magnesium oxide, and/or in the form of ion-leachable glasses, e.g., as described in U.S. Pat. Nos. 3,655,605, 3,814,717, 4,143,018, 4,209,434, 4,360,605 and 4,376,835.

The term "fluoride releasing glass(es)" refers to a glass capable to of releasing fluoride. Fluoride releasing capability may be provided by adding to a mixture of oxides for forming a glass inorganic particles containing fluoride with the proviso that the glass has fluoride releasability, preferably sustained fluoride releasability. Such inorganic particles may be selected from the group consisting of sodium fluoride, strontium fluoride, lanthanum fluoride, ytterbium fluoride, yttrium fluoride, and calcium-containing fluoroaluminosilicate glasses.

Preferably, the particulate glass filler is a reactive glass or a fluoride releasing glass as defined above, more preferably a reactive glass.

More preferably, the particulate glass filler is a reactive particulate glass filler comprising:
1) 20 to 45% by weight of silica,
2) 20 to 40% by weight of alumina,
3) 20 to 40% by weight of strontium oxide,
4) 1 to 10% by weight of $P_2O_5$, and
5) 3 to 25% by weight of fluoride.

The present curable dental two-pack composition preferably comprises 20 to 90 percent by weight of the particulate glass filler, more preferably 30 to 80 percent by weight, based on the total weight of the composition.

The particulate glass filler usually has an average particle size of from 0.005 to 100 µm, preferably of from 0.01 to 40 µm, more preferably of from 0.05 to 20 µm, most preferably of from 0.1 to 3 µm as measured, for example, by electron microscopy or by using a conventional laser diffraction particle sizing method as embodied by a MALVERN Mastersizer S or MALVERN Mastersizer 3000 apparatus.

The particulate glass filler may have a unimodal or multimodal (e.g., bimodal) particle size distribution, wherein a multimodal particulate glass filler represents a mixture of two or more particulate fractions having different average particle sizes.

More preferably, the particulate filler (c) not containing amino groups is a radiopaque filler. Suitable radiopaque particulate fillers may be selected from fillers containing elements of the group comprising tungsten, bismuth, strontium, barium, tantalum, cerium, tin, zirconium, ytterbium and yttrium.

The radiopaque particulate filler usually has an average particle size of from 0.005 to 100 µm, preferably of from 0.01 to 40 µm as measured using, for example, by electron microscopy or by using a conventional laser diffraction particle sizing method as embodied by a MALVERN Mastersizer S or MALVERN Mastersizer 2000 apparatus. The radiopaque particulate reactive glass may be a multimodal radiopaque particulate reactive glass representing a mixture of two or more radiopaque particulate fractions having different average particle sizes. The radiopaque particulate reactive glass may also be a mixture of particles of different chemical composition. In particular, it is possible to use a mixture of a radiopaque particulate reactive material and a radiopaque particulate non-reactive material.

The dental two-pack composition selected from a root canal sealing composition and a pulp capping composition according to the invention preferably comprises 1 to 80 percent by weight, more preferably 40 to 70 percent by weight, of the radiopaque particulate filler, based on the weight of the entire composition.

In a preferred embodiment, the cured dental two-pack composition has a $T_g$ of 60° C. or less.

In particularly preferred embodiments, the curable dental two-pack composition is a dental root canal sealer composition or a pulp capping composition.

Preferably, the curable dental two-pack composition is packaged in a two-barrel syringe.

A dental two-pack composition selected from a root canal sealing composition and a pulp capping composition may further contain catalyst systems and conventional additives such as stabilizers and pigments.

Suitable catalyst systems may contain an alkaline compound such as KOH, 1,4-diazabicydo[2.2.2]octane (DABCO), or 4-dimethylaminopyridine.

The present invention also provides a use of the crosslinker (a-1) having at least four primary amino groups for the preparation of a curable dental two-pack composition selected from a root canal sealing composition, and a pulp capping composition.

Examples

The present invention will be further illustrated with the following examples.

Materials

Polypropylene oxide biscyclocarbonate (PPO-BCC, $M_n$=450-500 g/mol, η=4.9 Pa*s at 23° C.) was purchased from Specific Polymers (France) and used as received. Cyclohexane-1,4-dimethanol diglycidylether was purchased from Carbosynth. PPO diglycidyl ether ($M_n$~ 640 g/mol) and hyperbranched polyethylene imine (hbPEI, $M_n$~ 600 g/mol, η=1.6 Pa*s at 23° C.) was purchased from Sigma Aldrich. Neopentyl glycol diglycidylether was purchased from abcr. Priamine 1071 was provided by Croda. Cyclohexane-1,4-dimethanol diglycidylether and N,N,N',N'-Tetrakis(3-aminopropyl)-1,4-butanediamine (TAPB) were purchased from Carbosynth (UK). $CaWO_4$ (1 µm and 6 µm Grade B) particles were purchased from Starck H.C. GmbH.

Aerosil$_{200}$ was provided by CSC Jäkle Chemie. All other chemicals were purchased from common chemical suppliers. SICOVIT® (Yellow 10 E 172) was purchased from Simon und Werner GmbH.

Methods

Gelation Time Measurement 1,3-dioxolan-2-one pastes and amine pastes were mixed (mixing ratio: 1,3-dioxolan-2-one paste:amine paste are given for each application example) on a mixing plate using a spatula. Mixing was applied for 30 s until a homogenous paste-paste-mixture was accomplished. The respective mass of the individual pastes was determined by means of a balance with an accuracy of ±0.0001 g. Approx. 1 mL of the paste-paste mixture was transferred into a glass vial (10 mL) with a round-cut plastic lid and glass bar. The glass bar needs to be in contact with the paste mixture. The vial was placed in an oil bath at 37° C. (to) with a temperature control [ΔT=±1° C.]. Gelation was achieved when rotation of the glass bar was no longer possible ($t_{gelation}$).

Synthesis of Polypropylene Bis(β-Amino Alcohol) (PPO-BAA)

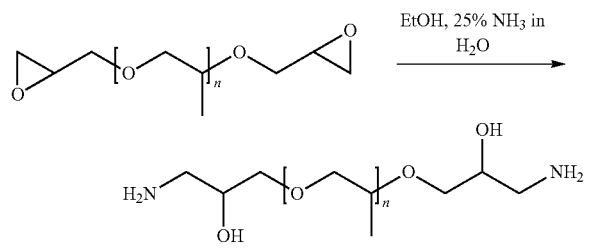

In an autoclave reactor (500 mL), PPO diglycidyl ether (50 g, 0.078 mol) was dissolved in ethanol (100 mL), and an ammonia solution (25 wt %, 220 mL, 39 eq.) was added. The autoclave reactor was sealed and the reaction was carried out for 24 h at 100° C. at an internal pressure of 4 to 5 bar. The sealed autoclave reactor was allowed to cool until the pressure decreased to 1.5 bar. Excess ammonia was carefully led through wash bottles with diluted sulfuric acid and the reaction mixture was transferred into a 500 mL flask. All volatiles were removed by means of a rotary evaporator under reduced pressure affording the pure product (yield: 99%) as yellow viscous oil. The viscosity was η=12.5 Pa*s at 23° C.

$^1$H NMR (400 MHz, DMSO-d$_6$): δ [ppm]=1.05 (CH$_3$—CH—), 2.30-2.70 (—CH$_2$—NH$_2$), 2.30-2.70 (—CH$_2$—NH$_2$), 3.20-4.00 (O—CH$_2$—CH—, O—CH$_2$—CH—, —NH$_2$, —OH).

Synthesis of Neopentyl Diglycidyl Biscyclocarbonate (NPDG-BCC)

Neopentyl glycol diglycidylether (31.2 g, 144.26 mmol, 30 mL) was stirred and cooled in a flask for 3 min using an ice bath and subsequently, tetrabutylammonium iodide (TBAI) (1.33 g, 3.61 mmol, 2.5 mol %) was added in small portions. The flask was sealed with a septum and cannula gas in- and outlets were installed. Carbon dioxide (CO$_2$) was bubbled through the mixture at 25° C. for 3 min and the CO$_2$-insertion was continued at 85° C. After complete conversion of epoxide moieties was revealed by $^1$H NMR spectroscopy, the reaction was stopped after 9 h. The product neopentyl diglycidyl biscyclocarbonate (NPDG-BCC) was recovered as a colorless viscous oil in quantitative yield. The viscosity was η=5.0 Pa*s at 23° C.

$^1$H NMR (400 MHz, CDCl$_3$): δ [ppm]=0.89 (CH$_3$), 2.30-2.70 (—CH$_2$—NH$_2$), 3.14-4.14 (—CH$_2$—NH$_2$), 4.33-4.60 (—(CO)O—CH—CH$_2$-0), 4.74-4.94 (—(CO)O—CH—CH$_2$—O).

Synthesis of cyclohexane-1,4-dimethanol biscyclocarbonate (CHDM-BCC)

Cyclohexane-1,4-dimethanol diglycidylether (59.9 g, 233.8 mmol, 54.5 mL) was stirred and cooled in a flask for 3 min using an ice bath and subsequently, tetrabutylammonium iodide (TBAI) (2.16 g, 5.85 mmol, 2.5 mol %) was added in small portions. The flask was sealed with a septum and cannula gas in- and outlets were installed. Carbon dioxide (CO$_2$) was bobbled through the mixture at 25° C. for 3 min and the CO$_2$-insertion was continued at 85° C. After complete conversion of epoxide moieties was revealed by $^1$H NMR spectroscopy, the reaction was stopped after 9 h. The product cyclohexane-1,4-dimethanol biscyclocarbonate (CHDM-BCC) was recovered as a colorless viscous oil in quantitative yield. The viscosity was η=34.0 Pa*s at 23° C.

$^1$H NMR (600 MHz, DMSO-d$_6$): δ [ppm]=4.91 (m, 2H, H13, H15), 4.51 and 4.24 (2×t, 4H, H14, H16), 3.88-3.18 (br. m, 8H, H7, H9, H11, H12), 1.81-1.61 and 1.54-1.24 (2×br. m, 8H, H1, H4, H3, H6), 0.97-0.81 (br. m, 2H, H2, H5)

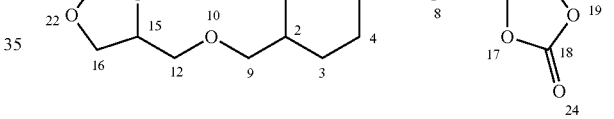

Application Example 1—Paste A.1. (Content of hbPEI in Amine Matrix: 25 wt %)

Preparation of 1,3-dioxolan-2-one Paste A1 (ASO3-129-01)

PPO-BCC (4.2762 g) was transferred into a speed mixer container and mixed for 1 min with 2150 rpm under reduced pressure (p=100 mBar). CaWO$_4$ (10.4733 g), Aerosil® 200 (0.1490 g) and SICOVIT® (Yellow 10 E172) (0.0382 g) were added and speed mixing was applied (1 min, 2150 rpm, 100 mBar). The paste was manually mixed with a spatula followed by another speed mixer run (1 min, 2150 rpm, 100 mBar) to afford a homogenous, light yellow paste. The viscosity of the paste is η=25.4±0.7 Pa*s at 23° C.

Preparation of Amine Paste A1 (ASO3-128-01)

hbPEI$_{600}$ (1.1183 g, 25 wt %) and PPO-BAA (3.3384 g) were transferred into a speed mixer container and mixed for 3 min with 2150 rpm under reduced pressure (p=1000 mBar). CaWO$_4$ (6.3329 g) and Aerosil®200 (0.1091 g) were added and speed mixing was applied (5 min, 2150 rpm, 1000 mBar). The paste was manually mixed with a spatula followed by another speed mixer run (1 min, 2150 rpm, 1000 mBar) to afford a homogenous, white paste. The viscosity of the paste is η=43.5±1.1 Pa*s at 23° C.

1,3-dioxolan-2-one Paste A1 and Amine Paste A1 were mixed in a ratio of 1:1.384 w(Amine Paste)/w(1,3-dioxolan-2-one Paste). The gel time at 37° C. is 2 h 10 min±10 min.

Application Example 2—Paste A.2. (Content of hbPEI in Amine Matrix: 20 wt %)

Preparation of 1,3-dioxolan-2-one Paste A2 (ASO3-135-01)

PPO-BCC (3.4309 g) was transferred into a speed mixer container and mixed for 1 min with 2150 rpm under reduced pressure (p=100 mBar). $CaWO_4$ (10.5852 g), Aerosil®200 (0.2862 g) and SICOVIT® (Yellow 10 E172) (0.0148 g) were added and speed mixing was applied (1 min, 2150 rpm, 100 mBar). The paste was manually mixed with a spatula followed by another speed mixer run (1 min, 2150 rpm, 100 mBar) to afford a homogenous, light yellow paste. The viscosity of the paste is $\eta=68.4\pm0.6$ Pa*s at 23° C.

Preparation of Amine Paste A2 (ASO3-134-01)

$hbPEI_{600}$ (0.7661 g, 20 wt %) and PPO-BAA (3.0658 g) were transferred into a speed mixer container and mixed for 3 min with 2150 rpm under reduced pressure (p=1000 mBar). $CaWO_4$ (6.0186 g) and Aerosil®200 (0.2011 g) were added and speed mixing was applied (5 min, 2150 rpm, 1000 mBar). The paste was manually mixed with a spatula followed by another speed mixer run (1 min, 2150 rpm, 1000 mBar) to afford a homogenous, white paste. The viscosity of the paste is $\eta=85.3\pm10.0$ Pa*s at 23° C.

1,3-dioxolan-2-one Paste A2 and Amine Paste A2 were mixed in a ratio of 1:1.439 w(Amine Paste)/w(1,3-dioxolan-2-one Paste). The gel time at 37° C. is 6 h 30 min±30 min.

Application Example 3—Paste B.1. (Content of hbPEI in Amine Matrix: 25 wt %)

Preparation of 1,3-dioxolan-2-one Paste B1 (ASO3-81-01)

PPO-BCC (1.7559 g) and NPDG-BCC (4.1078 g) were transferred into a speed mixer container and mixed for 1 min with 2150 rpm under reduced pressure (p=100 mBar). $CaWO_4$ (14.9768 g), Aerosil®200 (0.1900 g) and SICOVIT® (Yellow 10 E172) (0.0564 g) were added and speed mixing was applied (1 min, 2150 rpm, 100 mBar). The paste was manually mixed with a spatula followed by another speed mixer run (1 min, 2150 rpm, 100 mBar) to afford a homogenous, light yellow paste. The viscosity of the paste is $\eta=14.0\pm0.5$ Pa*s at 23° C.

Preparation of Amine Paste B1 (ASO3-80-01)

$hbPEI_{600}$ (1.5733 g, 25 wt %) and PPO-BAA (4.7209 g) were transferred into a speed mixer container and mixed for 3 min with 2150 rpm under reduced pressure (p=1000 mBar). $CaWO_4$ (8.529 g) and Aerosil®200 (0.1819 g) were added and speed mixing was applied (5 min, 2150 rpm, 1000 mBar). The paste was manually mixed with a spatula followed by another speed mixer run (1 min, 2150 rpm, 1000 mBar) to afford a homogenous, white paste. The viscosity of the paste is $\eta=30.6\pm1.7$ Pa*s at 23° C.

1,3-dioxolan-2-one Paste B1 and Amine Paste B1 were mixed in a ratio of 1:1.387 w(Amine Paste)/w(1,3-dioxolan-2-one Paste). The gel time at 37° C. is 4 h 46 min±15 min.

Application Example 4—Paste B.2. (Content of hbPEI in Amine Matrix: 30 wt %)

Preparation of 1,3-dioxolan-2-one Paste B2 (ASO3-84-01)

PPO-BCC (1.8183 g) and NPDG-BCC (4.2420 g) were transferred into a speed mixer container and mixed for 1 min with 2150 rpm under reduced pressure (p=100 mBar). $CaWO_4$ (13.8912 g), Aerosil®200 (0.1892 g) and SICOVIT® (Yellow 10 E172) (0.0540 g) were added and speed mixing was applied (1 min, 2150 rpm, 100 mBar). The paste was manually mixed with a spatula followed by another speed mixer run (1 min, 2150 rpm, 100 mBar) to afford a homogenous, light yellow paste.

Preparation of Amine Paste B2 (ASO3-83-01)

$hbPEI_{600}$ (1.8303 g, 30 wt %) and PPO-BAA (4.2700 g) were transferred into a speed mixer container and mixed for 3 min with 2150 rpm under reduced pressure (p=1000 mBar). $CaWO_4$ (9.4529 g) and Aerosil®200 (0.1818 g) were added and speed mixing was applied (5 min, 2150 rpm, 1000 mBar). The paste was manually mixed with a spatula followed by another speed mixer run (1 min, 2150 rpm, 1000 mBar) to afford a homogenous, white paste.

1,3-dioxolan-2-one Paste B1 and Amine Paste B1 were mixed in a ratio of 1:1.267 w(Amine Paste)/w(1,3-dioxolan-2-one Paste). The gel time at 37° C. is 2 h 34 min±10 min.

Application Example 5—Paste C.1. (Content of TAPB in Amine Matrix: 30 wt %)

Preparation of 1,3-dioxolan-2-one Paste C1 (ASO4-135-02)

CHDM-BCC (2.336 g) was transferred into a speed mixer container and mixed for 1 min with 2150 rpm under reduced pressure (p=100 mBar). $CaWO_4$ (Grade B) (7.0550 g), Aerosil®$_{200}$ (0.0953 g) and SICOVIT® (Yellow 10 E172) (0.0091 g) were added and speed mixing was applied (1 min, 2150 rpm, 100 mBar). The paste was manually mixed with a spatula followed by another speed mixer run (1 min, 2150 rpm, 100 mBar) to afford a homogenous, light yellow paste.

Preparation of Amine Paste C1 (ASO4-135-01)

N,N,N',N'-Tetrakis(3-aminopropyl)-1,4-butanediamine (TAPB) (0.5443 g, 30 wt %) and Priamine 1071 (1.2710 g) ($\eta$ of amine resin mixture at 23° C. was 0.387 Pa*s, SAR3-83-01) were transferred into a speed mixer container and mixed for 1 min with 2150 rpm under reduced pressure (p=1000 mBar). $CaWO_4$ (Grade B) (6.632 g) and Aerosil®$_{200}$ (0.0862 g) were added and speed mixing was applied (1 min, 2150 rpm, 1000 mBar). The paste was manually mixed with a spatula followed by another speed mixer run (1 min, 2150 rpm, 1000 mBar) to afford a homogenous, white paste.

1,3-dioxolan-2-one Paste C.1 and Amine Paste C.1 were mixed in a ratio of 1.0627:1 w(1,3-dioxolan-2-one Paste)/w(Amine Paste). The gelation time at 37° C. was 1 h 20 min (ASO4-153-03). Flow: 19.2 mm, film thickness: 13 µm (according to ISO6876:2012) (ASO4-160-01).

It will be understood that the embodiments described herein are merely exemplary and that a person skilled in the art may make many variations and modifications without departing from the spirit and scope of the invention. All such variations and modifications, including those discussed above, are intended to be included within the scope of the invention as defined by the appended claims.

The invention claimed is:

1. A curable dental two-pack composition comprising:
   (a) a first paste comprising (a-1) one or more crosslinkers comprising a hyberbranched polyethene imine, a 1,2,3,4,5,6-hexanehexamine, a 1,2,3,4,5-pentanepentamine, or a mixture thereof; and
   (b) a second paste comprising (b-1) one or more compounds polymerizable with a crosslinker of the first paste in a step-growth polymerization reaction, which compounds have at least two 1,3-dioxolan-2-one groups selected from the following formula (A) and (B) attached to or connected by one or more organic groups:

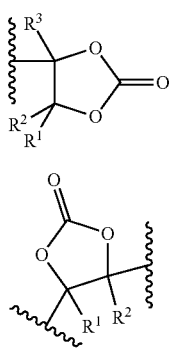

wherein $R^1$, $R^2$ and $R^3$, which are independent from each other, represent a hydrogen atom or a $C_{1-6}$ alkyl group, wherein at least one of $R^1$, $R^2$ and $R^3$ is a $C_{1-6}$ alkyl group.

2. The curable dental two-pack composition according to claim 1, wherein the first paste further comprises:
   (a-2) one or more compounds having two groups selected from primary and secondary amino groups.

3. The curable dental two-pack composition according to claim 1 further comprising:
   (c) a particulate filler not containing amino groups.

4. The curable dental two-pack composition according to claim 3, further comprising:
   (c) a radioopaque filler.

5. The curable dental two-pack composition according to claim 1, wherein the one or more crosslinkers (a-1) are linear or branched.

6. The curable dental two-pack composition according to claim 2, wherein the molar ratio of the 1,3-dioxolan-2-one groups (A, B) in component (b-1) in the second paste to the primary amino groups in component (a-1) and (a-2) in the first paste [1,3-dioxolan-2-one groups$_{(b-1)}$]/[primary amino groups$_{(a-1),(a-2)}$] is in the range of from 0.9 to 1.1.

7. The curable dental two-pack composition according to claim 5, wherein the first paste and the second paste are mixed in equal volumes.

8. The curable dental two-pack composition according to claim 2, which contains the one or more compounds having two groups selected from primary and secondary amino groups (a-2) in an amount of from 1 to 40 percent by weight based on the total weight of the composition.

9. The curable dental two-pack composition according to claim 1, which contains the one or more compounds polymerizable with the crosslinker (b-1) in an amount of from 1 to 40 percent by weight based on the total weight of the composition.

10. The curable dental two-pack composition according to claim 1, wherein the cured composition has a $T_g$ of 60° C. or less.

11. The curable dental two-pack composition according to claim 1, which is a dental root canal sealer composition or a pulp capping composition.

12. The curable dental two-pack composition according to claim 1, which is packaged in a two-barrel syringe.

13. The curable dental two-pack composition according to claim 1, wherein (b-1) the compound polymerizable with the crosslinker compounds is a compound of the following formula (II):

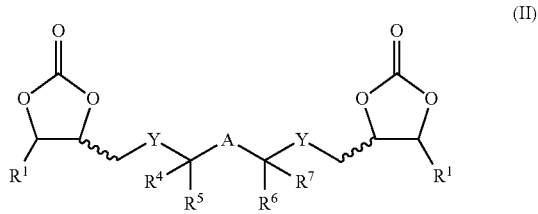

wherein
A is a hydrocarbon group which may contain one or more hetero atoms selected from oxygen and sulfur atoms;
$R^1$ is a $C_{1-6}$ alkyl group;
$R^4$, $R^5$, $R^6$ and $R^7$ are independent from each other and represent a hydrogen atom or a methyl group and
the Y, which are independent from each other represent a single bond, an oxygen atom, a sulfur atom, an ester bond or a urethane bond.

14. The curable dental two-pack composition according to claim 1, wherein the first paste comprises a hyperbranched polyethylene imine.

15. The curable dental two-pack composition according to claim 14, wherein the first paste has a viscosity in the range of 0.1 to 25 Pa*s at 23° C.

* * * * *